(12) United States Patent
Tanner et al.

(10) Patent No.: US 10,426,170 B2
(45) Date of Patent: Oct. 1, 2019

(54) COMPOSITIONS AND METHODS FOR REDUCING INFESTATION OF WEEDS OR UNWANTED PLANTS WHILE MINIMIZING INJURY OR DAMAGE TO PLANTS OR CROPS

(71) Applicant: BAYER CROPSCIENCE LP, Research Triangle Park, NC (US)

(72) Inventors: David Tanner, Chapel Hill, NC (US); James Bloomberg, Morrisville, NC (US); Stephen M Irons, Mahomet, IL (US); John Hinz, Story City, IA (US)

(73) Assignee: BAYER CROPSCIENCE LP, St. Louis, MO (US)

( * ) Notice: Subject to any disclaimer, the term of this patent is extended or adjusted under 35 U.S.C. 154(b) by 8 days.

(21) Appl. No.: 15/559,350

(22) PCT Filed: Mar. 24, 2016

(86) PCT No.: PCT/US2016/024011
§ 371 (c)(1),
(2) Date: Sep. 18, 2017

(87) PCT Pub. No.: WO2016/154436
PCT Pub. Date: Sep. 29, 2016

(65) Prior Publication Data
US 2018/0103644 A1    Apr. 19, 2018

Related U.S. Application Data

(60) Provisional application No. 62/138,019, filed on Mar. 25, 2015.

(51) Int. Cl.
*A01N 57/20* (2006.01)
*A01N 41/06* (2006.01)
*A01N 41/10* (2006.01)
*A01N 43/40* (2006.01)
*A01N 43/80* (2006.01)

(52) U.S. Cl.
CPC ............. *A01N 57/20* (2013.01); *A01N 41/06* (2013.01); *A01N 41/10* (2013.01); *A01N 43/40* (2013.01); *A01N 43/80* (2013.01)

(58) Field of Classification Search
None
See application file for complete search history.

(56) References Cited

PUBLICATIONS

International Search Report for PCT/US2016/024011, dated May 19, 2016.

*Primary Examiner* — Alton N Pryor
(74) *Attorney, Agent, or Firm* — McBee Moore Woodward & Vanik IP, LLC

(57) ABSTRACT

The disclosure provides for methods and compositions capable of controlling or reducing the infestation of weeds or unwanted plants, the compositions containing HPPD inhibitor herbicide, glyphosate, and fomesafen. The disclosure further provides for methods and compositions capable of controlling or reducing the infestation of weeds or unwanted plants, increasing the yield of plants or crops, and reducing the injury of plants or crops. Seeds, plants, and plant parts treated with compositions described herein are also provided for by the disclosure.

19 Claims, 7 Drawing Sheets

FIG. 1A

| Test No. | Treatment. | Formulation | | Dose | | Appl. | Timing/Application | |
|---|---|---|---|---|---|---|---|---|
| 1 | UNTREATED WEED FREE | -- | | | | | | |
| 1 | ROUNDUP® POWER MAX | 660 | GA/L | SL | 1543 | G A/HA | EAPOCR | A |
| 1 | AMMONIUM SULFATE | 100 | %AW/W | SG | 2852 | G A/HA | EAPOCR | A |
| 1 | ROUNDUP® POWER MAX | 660 | GA/L | SL | 1543 | G A/HA | POSPOS | B |
| 1 | AMMONIUM SULFATE | 100 | %AW/W | SG | 2852 | G A/HA | POSPOS | B |
| 2 | BALANCE BEAN | 480 | GA/L | SC | 4.375 | G A/HA | EAPOCR | A |
| 2 | ROUNDUP® POWER MAX | 660 | GA/L | SL | 1543 | G A/HA | EAPOCR | A |
| 2 | AMMONIUM SULFATE | 100 | %AW/W | SG | 2852 | G A/HA | EAPOCR | A |
| 2 | ROUNDUP® POWER MAX | 660 | GA/L | SL | 1543 | G A/HA | POSPOS | B |
| 2 | AMMONIUM SULFATE | 100 | %AW/W | SG | 2852 | G A/HA | POSPOS | B |
| 3 | BALANCE BEAN | 480 | GA/L | SC | 2.2 | G A/HA | EAPOCR | A |
| 3 | ROUNDUP® POWER MAX | 660 | GA/L | SL | 1543 | G A/HA | EAPOCR | A |
| 3 | AMMONIUM SULFATE | 100 | %AW/W | SG | 2852 | G A/HA | EAPOCR | A |
| 3 | ROUNDUP® POWER MAX | 660 | GA/L | SL | 1543 | G A/HA | POSPOS | B |
| 3 | AMMONIUM SULFATE | 100 | %AW/W | SG | 2852 | G A/HA | POSPOS | B |

FIG. 1B

| Test No. | Treatment. | Formulation | | Dose | | Appl. | Timing/Application | |
|---|---|---|---|---|---|---|---|---|
| 4 | BALANCE BEAN | 480 | GA/L | SC | 1.1 | G A/HA | EAPOCR | A |
| 4 | ROUNDUP® POWER MAX | 660 | GA/L | SL | 1543 | G A/HA | EAPOCR | A |
| 4 | AMMONIUM SULFATE | 100 | %AW/W | SG | 2852 | G A/HA | EAPOCR | A |
| 4 | ROUNDUP® POWER MAX | 660 | GA/L | SL | 1543 | G A/HA | POSPOS | B |
| 4 | AMMONIUM SULFATE | 100 | %AW/W | SG | 2852 | G A/HA | POSPOS | B |
| 5 | BALANCE BEAN | 480 | GA/L | SC | 0.55 | G A/HA | EAPOCR | A |
| 5 | ROUNDUP® POWER MAX | 660 | GA/L | SL | 1543 | G A/HA | EAPOCR | A |
| 5 | AMMONIUM SULFATE | 100 | %AW/W | SG | 2852 | G A/HA | EAPOCR | A |
| 5 | ROUNDUP® POWER MAX | 660 | GA/L | SL | 1543 | G A/HA | POSPOS | B |
| 5 | AMMONIUM SULFATE | 100 | %AW/W | SG | 2852 | G A/HA | POSPOS | B |
| 6 | BALANCE BEAN | 480 | GA/L | SC | 0.275 | G A/HA | EAPOCR | A |
| 6 | ROUNDUP® POWER MAX | 660 | GA/L | SL | 1543 | G A/HA | EAPOCR | A |
| 6 | AMMONIUM SULFATE | 100 | %AW/W | SG | 2852 | G A/HA | EAPOCR | A |
| 6 | ROUNDUP® POWER MAX | 660 | GA/L | SL | 1543 | G A/HA | POSPOS | B |
| 6 | AMMONIUM SULFATE | 100 | %AW/W | SG | 2852 | G A/HA | POSPOS | B |

FIG. 1C

| Test No. | Treatment. | Formulation | | Dose | | Appl. | Timing/Application | |
|---|---|---|---|---|---|---|---|---|
| 7 | BALANCE BEAN | 480 | GA/L | SC | 0.14 | G A/HA | EAPOCR | A |
| 7 | ROUNDUP® POWER MAX | 660 | GA/L | SL | 1543 | G A/HA | EAPOCR | A |
| 7 | AMMONIUM SULFATE | 100 | %AW/W | SG | 2852 | G A/HA | EAPOCR | A |
| 7 | ROUNDUP® POWER MAX | 660 | GA/L | SL | 1543 | G A/HA | POSPOS | B |
| 7 | AMMONIUM SULFATE | 100 | %AW/W | SG | 2852 | G A/HA | POSPOS | B |
| 8 | BALANCE BEAN | 480 | GA/L | SC | 0.07 | G A/HA | EAPOCR | A |
| 8 | ROUNDUP® POWER MAX | 660 | GA/L | SL | 1543 | G A/HA | EAPOCR | A |
| 8 | AMMONIUM SULFATE | 100 | %AW/W | SG | 2852 | G A/HA | EAPOCR | A |
| 8 | ROUNDUP® POWER MAX | 660 | GA/L | SL | 1543 | G A/HA | POSPOS | B |
| 8 | AMMONIUM SULFATE | 100 | %AW/W | SG | 2852 | G A/HA | POSPOS | B |
| 9 | BALANCE BEAN | 480 | GA/L | SC | 0.0375 | G A/HA | EAPOCR | A |
| 9 | ROUNDUP® POWER MAX | 660 | GA/L | SL | 1543 | G A/HA | EAPOCR | A |
| 9 | AMMONIUM SULFATE | 100 | %AW/W | SG | 2852 | G A/HA | EAPOCR | A |
| 9 | ROUNDUP® POWER MAX | 660 | GA/L | SL | 1543 | G A/HA | POSPOS | B |
| 9 | AMMONIUM SULFATE | 100 | %AW/W | SG | 2852 | G A/HA | POSPOS | B | ered herein are HPPD inhibitor herbicide, glyphosate, and fomesafen. The
COMPOSITIONS AND METHODS FOR REDUCING INFESTATION OF WEEDS OR UNWANTED PLANTS WHILE MINIMIZING INJURY OR DAMAGE TO PLANTS OR CROPS

CROSS REFERENCE TO RELATED APPLICATION

This application is a 371 National Stage Application of PCT/US16/24011, filed Mar. 24, 2016, which claims the benefit of U.S. Provisional Application Ser. No. 62/138,019, filed Mar. 25, 2015, the contents of which are herein incorporated by reference in their entireties.

FIELD

The disclosure provides for methods and compositions capable of controlling or reducing the infestation of weeds or unwanted plants. In an aspect, the composition(s) contain HPPD inhibitor herbicide, glyphosate, and fomesafen. The disclosure further provides for methods and compositions capable of controlling or reducing the infestation of weeds or unwanted plants, increasing the yield of plants or crops, and reducing the injury of plants or crops by utilizing one or more compositions described herein. Seeds, plants, and plant parts treated with compositions described herein are also provided for by the disclosure.

BACKGROUND

There is a need to develop compositions and/or methods that are capable of improving, controlling, and/or reducing infestion of weeds or unwanted plants while minimizing injury to crops and plants. Herbicidal treatment of plants, particularly crop plants, can significantly increase crop plant yields and improve the heartiness of the crop plant by removing other vegetation competing for food and water. However, as herbicides operate to eliminate or reduce weeds or other unwanted plants in the area of the crop plant, it is sometimes the case that the herbicide being applied to enhance the plants growth and strength, operates to harm or weaken the very crop plant it was intended to help.

Efforts have been made to produce plants that are resistant to herbicides. Efforts have also been made in the art to develop herbicides which are "safened," which generally means that the herbicide is formulated in such a way that it will not hurt the crop plant while still eliminating the weeds surrounding the crop plant. However, there remains a need in the art for new and improved ways of treating plants, particularly crop plants, with herbicides to enhance their strength, growth and yield, yet not damaging or otherwise injuring the crop plant with the herbicide.

Here, compositions, seeds, plants, and methods are provided that reduce or control weeds or unwanted plant infestation while reducing plant or crop injury which may also lead to increased plant or crop yields.

SUMMARY

In an aspect, the disclosure provides for methods for controlling, mitigating, or reducing weed infestation and/or damage in a glyphosate tolerant or resistant seeds, plants, or crops, comprising treating soil, a plant, and/or a plant part with one or more compositions comprising:

a) a HPPD inhibitor herbicide;
b) glyphosate; and
c) fomesafen.

The disclosure further provides for methods which results in (1) increased control or reduction of weed infestation, (2) reduced injury or damage to plants or crops, and/or (3) increased in crop or plant yield relative to the application of a HPPD inhibitor herbicide and glyphosate.

In another aspect, the disclosure provides for methods described herein, wherein about 0.01 to about 5 g ai/ha, about 0.01 to about 2 g ai/ha, or about 0.03 to about 0.5 g ai/ha of a HPPD inhibitor herbicide, for example, isoxaflutole, is applied to soil, a plant, or plant part.

The disclosure also provides for a treated soil, treated plant part, or treated plant comprising.

a) a HPPD inhibitor herbicide;
b) glyphosate; and
c) fomesafen.

The use of a composition comprising:

a) a HPPD inhibitor herbicide;
b) glyphosate; and
c) fomesafen;

wherein said composition controls, mitigates, or reduces weed infestation and/or damage in a glyphosate tolerant or resistant seed, plant, or crop is also provided for in an aspect.

The disclosure further provides for an aspect wherein the HPPD inhibitor herbicide is selected from the group consisting of mesotrione, tembotrione, isoxaflutole, and bicyclopyrone.

BRIEF DESCRIPTION OF THE FIGURES

FIGS. 1A through 1C set forth nine different treatment trials applied to glyphosate tolerant soybean seeds.

DETAILED DESCRIPTION

Figure 2:
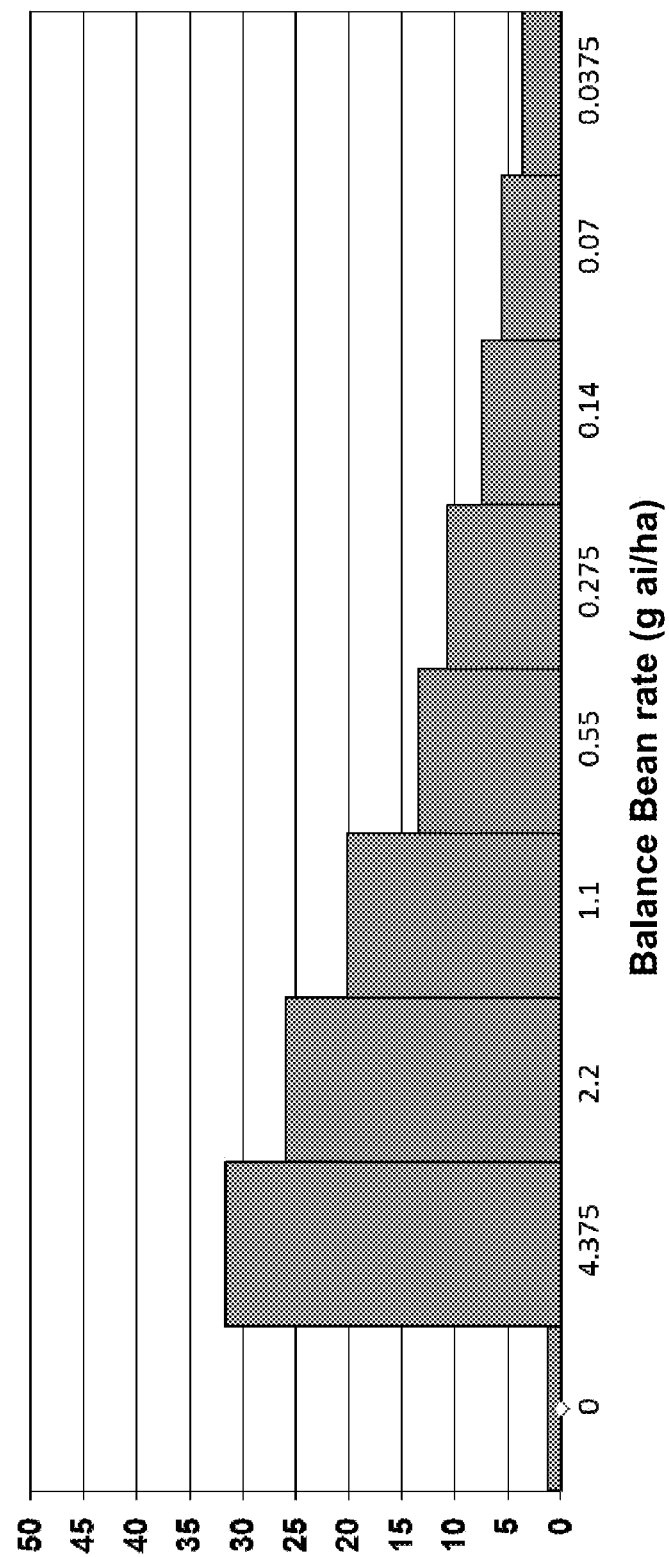
FIG. 2 sets forth the maximum phytotoxicity for Roundup® Ready soybean seeds treated with a Balance® Bean and Roundup® at V2. The data represents the average of six trials. Max phytotoxicity (%) is represented in the Y axis.

The disclosure provides for compositions, seeds, plants, and methods for controlling, mitigating, or reducing weed infestation and/or damage.

In an aspect, the disclosure provides for compositions, seeds, plants, and methods for controlling, mitigating, or reducing weed infestation and/or damage while minimizing or reducing plant damage.

In another aspect, disclosure provides for compositions, seeds, plants, and methods for controlling, mitigating, or reducing weed infestation and/or damage while also increasing or maintaining plant or crop yield.

The disclosure also provides for compositions, seeds, plants, and methods for
  (1) controlling, mitigating, or reducing weed infestation and/or damage;
  (2) increasing or maintaining plant or crop yield; and
  (3) minimizing or reducing plant damage.

The disclosure provides for compositions, seeds, plants, and methods for controlling, mitigating, or reducing weed infestation and/or damage, comprising crops comprising treating a plant, crop, seed, or plant part with a composition comprising an hydroxyphenylpyruvate dioxygenase (abbreviated herein as HPPD) inhibitor herbicide, for example, isoxaflutole.

In an aspect, the disclosure provides for compositions, seeds, plants, and methods for controlling, mitigating, or reducing weed infestation and/or damage, comprising treating a single, double, or triple herbicidal trait resistant plant, crop, seed, or plant part with a composition comprising one or more of isoxaflutole, glyphosate, and/or isoxaflutole.

The disclosure also provides for compositions, seeds, plants, and methods for controlling, mitigating, or reducing weed infestation and/or damage, comprising treating a glyphosate resistant plant, crop, seed, or plant part with a composition comprising isoxaflutole and glyphosate. In another aspect, the disclosure provides for compositions, seeds, plants, and methods for controlling, mitigating, or reducing weed infestation and/or damage, comprising treating a glyphosate resistant plant, crop, seed, or plant part with a first composition comprising isoxaflutole and a second composition comprising glyphosate.

In an aspect, the disclosure provides for compositions, seeds, plants, and methods for controlling, mitigating, or reducing weed infestation and/or damage, comprising treating a glyphosate resistant plant, crop, soil, or plant part with a composition comprising isoxaflutole, glyphosate, and fomesafen a salt thereof. In another aspect, the disclosure provides for compositions, seeds, plants, and methods for controlling, mitigating, or reducing weed infestation and/or damage, comprising treating a glyphosate resistant plant, crop, or plant part with a first composition comprising isoxaflutole a second composition glyphosate, and a third composition comprising fomesafen or a salt thereof. In yet another aspect, the disclosure provides for compositions, seeds, plants, and methods for controlling, mitigating, or reducing weed infestation and/or damage, comprising crops comprising treating a glyphosate resistant plant, crop, or plant part with a first composition comprising isoxaflutole and a second composition comprising glyphosate and fomesafen and/or a salt thereof. In another aspect, isoxaflutole, glyphosate, and fomesafen are applied as a single composition, two compositions, or three compositions. Additional components described herein may also be added to the aforementioned compositions in an aspect.

In another aspect, the disclosure provides for compositions, seeds, plants, and methods for controlling, mitigating, or reducing weed infestation and/or damage, comprising treating an isoxaflutole and glyphosate resistant or tolerant plant, crop, seed, or plant part with a composition comprising isoxaflutole and glyphosate. In another aspect, the disclosure provides for compositions, seeds, plants, and methods for controlling, mitigating, or reducing weed infestation and/or damage, comprising treating an isoxaflutole and glyphosate resistant or tolerant plant, crop, seed, or plant part with a composition comprising isoxaflutole and glyphosate, crop, seed, or plant part with a first composition comprising isoxaflutole and a second composition glyphosate.

In an aspect, the disclosure provides for compositions, seeds, plants, and methods for controlling, mitigating, or reducing weed infestation and/or damage, comprising treating an isoxaflutole and glyphosate resistant or tolerant plant, crop, seed, or plant part with a composition comprising isoxaflutole, glyphosate, and fomesafen and/or a salt thereof. In another aspect, the disclosure provides for compositions, seeds, plants, and methods for controlling, mitigating, or reducing weed infestation and/or damage, comprising treating an isoxaflutole and glyphosate resistant or tolerant plant, crop, seed, or plant part with a first composition comprising isoxaflutole a second composition glyphosate, and a third composition comprising fomesafen or a salt thereof. In another aspect, isoxaflutole, glyphosate, and fomesafen are applied as a single composition, two compositions, or three compositions. Additional components described herein may also be added to the aforementioned compositions in an aspect.

In addition to controlling, mitigating, or reducing weed infestation, in another aspect the disclosure provides for controlling, mitigating, or reducing another unwanted plants or grass described herein. In another aspect, in additional to controlling, mitigating, or reducing weed infestation, compositions or methods described herein increase or maintain yield and maintain or reduce damage to a plant, crop, seed, or plant part.

In an aspect, a composition described herein is applied to the crop, plant, or plant part at the V2 stage. In another aspect, a composition describing one or more of isoxaflutole, glyphosate, and fomesafen are applied to the crop, plant, or plant part at the V2 stage. In another aspect, a composition describing one or more of isoxaflutole, glyphosate, and fomesafen are applied to the crop, plant, or plant part at the V2 stage.

In another aspect, a composition described herein is applied to a crop, plant, or plant part in a single application at the V2 stage and at another time during the growing process. In another aspect, a composition described herein is applied to the crop, plant, or plant part in a single application at the V2 stage, so long as the application amount does not exceed 105 grams per season of Balance® Bean. In another aspect, a composition described herein, for example Balance® Bean, is applied in two, three, four, or five application steps so long as the total application Balance® Bean does not exceed 105 grams of active per growing season.

In another aspect, a HPPD inhibitor herbicide described herein, such as isoxaflutole, is applied to a crop, plant, plant part, and/or soil with or without an additional composition, such as a glyphosate composition. In another aspect, an composition described herein, for example a glyphosate composition, is applied in one, two, three, or four or more steps or on the basis of need where weeds or unwanted plants are present.

In another aspect, the disclosure provides for a method of controlling, mitigating, or reducing weed infestation by applying one or more compositions to a plant, crop, seed, or plant part during one or more of burndown, preemergence, and/or early post-emergence.

In another aspect, the disclosure provides for pre-plant, pre-emergent, post-emergent, application steps or combinations thereof. In another aspect, a compound or composition described herein is first applied in a pre-plant step and followed by one or more pre-emergent or post-emergent steps. In yet another aspect, the disclosure provides for only a pre-plant step.

In an aspect, compositions described herein can be applied in a known manner, for example together (for example as a coformulation or as a tank mix), or else as a time-split application, for example to the plants, parts of plants, plant seeds or to the area on which the plants grow. It is possible, for example, to apply the individual active compounds or herbicides described herein in combination or in a plurality of portions (sequential application), for example as pre-emergence applications followed by post-emergence applications or as early post-emergence applications followed by applications at medium or late post-emergence. In another aspect, the disclosure provides for simultaneous or nearly simultaneous application of one or more compositions described herein.

The disclosure provides for an aspect wherein post-emergent or pre-emergent methods of application are used. By the term "pre-emergent" is meant that the composition is applied before a green plant has emerged from the ground. A pre-emergent herbicide application may take place at the time of planting of the seed, or before or after planting. By the term "post-emergent" is meant a composition is applied to the foliage and ground after the plant has emerged from the ground. In the case of monocotyledons, the application of herbicide can occur over a broad range of above-ground growth stages, but is generally applied between the 2, 3, 4, or 5-leaf stage.

In an aspect, a composition described herein is applied to soil, plants, crops, seeds, or plant parts thereof in a single application step. In another aspect, a composition described herein is applied to plants, crops, seeds, or plant parts thereof in multiple application steps, for example, two, three, four, five or more application steps. In another aspect, the second, third, fourth, or fifth or more application steps may be with the same or different compositions. The methods described herein also provide for an aspect where multiple application steps are excluded.

In an aspect, one or more compositions described herein are applied in only a single application step. In yet an aspect, one or more compositions described herein are applied in only a single applications step between the 2, 3, 4, or 5-leaf stage. In yet another aspect, one or more compositions described herein are applied in only a single application step at V2 or 2 leaf stage.

In another aspect, a composition described herein is applied to soil, plants, crops, or plant parts thereof at the time of planting to about 30 minutes, about 30 minutes to about 1 hour, about 1 hour to about 4 hours, about 4 hours to about 12 hours, about 1 hour to about 1 day, about 1 day to about 5 days, about 5 days to about 10 days, about 10 days to about 20 days, about 10 days to about 50 days, about 20 days to about 50 days, about 35 to about 50 days or any combination thereof. In yet another aspect, a composition described herein is applied to soil, plants, crops, or plant parts thereof in one or more application intervals of about 30 minutes, about 1 hour, about 2 hours, about 6 hours, about 8 hours, about 12 hours, about 1 day, about 5 days, about 7 days, about 10 days, about 12 days, about 14 days, about 21 days, about 28 days, about 35 days, about 45 days, or about 50 days.

In another aspect, a composition described herein is applied to soil, plants, crops, or plant parts thereof (1) at the time of planting to about 1 hour after planting and (2) at about 30 to about 50 days, about 25 to about 40 days, or about 25 to about 35 days after planting, for example, as a side dress.

In an aspect, a composition described herein is applied to a plant, crop, or plant part thereof one or more times during a growing, planting, or harvesting season. In another aspect, a compound or composition described herein is applied to a plant, crop, or plant part thereof in one, two, three, four, or five or more times during a growing, planting, or harvesting season. In another aspect, a compound or composition described herein is applied to a plant, crop, or plant part thereof only one time, no more than two times, or no more than three times during a growing, planting, or harvesting season.

In another aspect, a compound or composition described herein is applied to soil, plants, crops, or plant parts thereof in an application regimen at about 1 hour to about 3 hours after the first application and followed by a second application at about 3 hours to about 6 hours; at about 1 hour to about 3 hours after the first application and followed by a second, third, or fourth application at about 12 hours to about 24 hours about 1 to about 7 days after the first application and followed by a second application at about 10 to about 14 days.

In a further aspect, the disclosure provides for a method of controlling damage, reducing damage, and/or increasing plant yield comprising a plant drench application of a composition comprising, consisting essentially of, or consisting of isoxaflutole together with one or more of an active agent described herein as a plant drench application.

Method described herein can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down-regulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

In an aspect, plants can be obtained by traditional breeding and optimization methods or by biotechnological and recombinant methods, or combinations of these methods, including the transgenic plants and including the plant varieties which are capable or not capable of being protected by Plant Breeders' Rights.

In another aspect, plant species and plant varieties which are found in the wild or which are obtained by traditional biological breeding methods, such as hybridization or protoplast fusion, and parts of these species and varieties are treated. In a further preferred embodiment, transgenic plants and plant varieties which were obtained by recombinant methods, if appropriate in combination with traditional methods (genetically modified organisms) and their parts are treated.

Plant parts should be understood as meaning all above ground and subsoil parts and organs of plants, such as shoot, leaf, flower, root, leaves, needles, stalks, stems, fruiting bodies, fruits and seeds, tubers and rhizomes. Plant parts also include harvested crops, and also vegetative and generative propagation material, for example cuttings, tubers, rhizomes, slips and seeds.

Plant parts, plants, and soil may be treated with the described compositions by applying the compounds or compositions directly to soil, a plant part, or a plant. In another aspect, the plant part or plant may be treated indirectly, for example by treating the environment or habitat in which the seed, plant part, or plant is exposed to. Conventional treatment methods may be used to treat the environment or habitat including dipping, spraying, fumigating, chemigating, fogging, scattering, brushing on, shanking or injecting.

According to the invention the treatment of a plant or plant part with a composition described herein can be carried out directly by the customary treatment methods, for example by immersion, spraying, vaporizing, fogging, injecting, dripping, drenching, and broadcasting or painting In yet another aspect, a weed, grass, or unwanted plant described herein is selected from the group consisting of grass, annual grass, woolly cupgrass, barnyardgrass, signalgrass, crabgrass, foxtail grass, giant grass, green grass, yellow grass, goosegrass, johnsongrass, panicum, fall grass, panicum, Texas grass, broadleaf weeds, perennial weeds, annual and perennial monocotyledonous or dicotyledonous weeds, Milkweed Climbing, Milkweed Honeyvine, Bindweed Field, Bindweed, Hedge, Trumpetcreeper glyphosate-, triazine-, PPO- and ALS-resistant weeds, such as resistant marestail, common ragweed, waterhemp, and black nightshade, and palmer amaranth.

The disclosure provides for a method of reducing plant, root, or plant part damage by treating soil, a plant, root, and/or plant part with one of more compositions described herein. The disclosure provides for a method of reducing plant, root, or plant part damage by treating soil, a plant, root, and/or plant part with a composition including an herbicide, for example, isoxaflutole, glyphosate, and/or fomesafen.

In an aspect, the disclosure provides for decreased plant or crop damage when one or more compositions comprising isoxaflutole, glyphosate, and fomesafen are applied to a single, double, or triple herbicidal trait resistant plant, crop, or plant part. In an aspect, disclosure provides for decreased plant or crop damage when a composition(s) comprising isoxaflutole, glyphosate, and fomesafen are applied to a single, double, or triple herbicidal trait resistant plant, crop, or plant part is relative to treatment with only isoxaflutole and glyphosate. That is, in an aspect, the addition of a combination of glyphosate and fomesafen with isoxaflutole unexpectedly provides for a safening influence as compared to the application of glyphosate and isoxaflutole. Such a result is unexpected as the addition of three components, such as of isoxaflutole, glyphosate, and fomesafen, would have the expected result of increasing plant or crop damage when applied to a plant, crop, or plant part as compared to the application of a two component application, for example, such as glyphosate and isoxaflutole. This unexpected finding is further reflected in FIGS. 2, 3, 4, and 5 described herein. For example, in FIG. 4, yields were higher when a (1) composition comprising isoxaflutole, for example Balance® Bean, was used in combination with (2) a composition comprising both glyphosate and fomesafen, for example, Flexstar® GT as compared to a composition with glyphosate but without fomesafen, for example, Roundup®, as in FIG. 5. Based on this observation, Flexstar® appears to safen soybeans from Balance® Bean yield reduction.

The disclosure further provides for a reduction in plant or crop damage by a composition, composition combination, or method described herein, wherein the composition, composition combination, or method reduces plant, root, or plant part damage by about 5%, about 10%, about 20%, about 25%, about 40%, about 50%, about 60%, or about 75%. In an aspect, the disclosure provides for decreased plant or crop damage when a composition(s) comprising isoxaflutole, glyphosate, and fomesafen are applied to a single, double, or triple herbicidal trait resistant plant, crop, seed, or plant part is reduced by about 5%, about 10%, about 20%, about 25%, about 40%, about 50%, about 60%, or about 75% relative to treatment with only glyphosate and isoxaflutole. In yet another aspect, the disclosure further provides for a synergistic combination of isoxaflutole, glyphosate, and isoxaflutole that does not reduce or increases plant or crop damage by about 5%, 10%, 15%, or 25% relative treatment with only glyphosate and isoxaflutole. Even if no reduction or a slight increase in plant damage is observed, in certain aspects, such an observation may still be unexpected as the combination of three components, such as isoxaflutole, glyphosate, and fomesafen may have been expected to inflict addition damage to a plant or crop.

The disclosure also provides for an increased plant or crop yield, wherein a composition, composition combination, or method described herein increases plant or crop yield by about 5%, about 10%, about 20%, about 25%, about 40%, about 50%, about 60%, or about 75%. In an aspect, the disclosure provides for an increased plant or crop yield, when one or more compositions comprising isoxaflutole, glyphosate, and fomesafen are applied to a single, double, or triple herbicidal trait resistant plant, crop, seed, or plant part is reduced by about 5%, about 10%, about 20%, about 25%, about 40%, about 50%, about 60%, or about 75% relative to treatment with only glyphosate and isoxaflutole.

In an aspect, the disclosure provides for a composition comprising, consisting essentially of, or consisting of a HPPD inhibitor herbicide for use with any of the methods described herein. Non-limiting examples of HPPD inhibitor herbicides include active agents in the class of isoxazoles, diketonitriles, triketones and/or pyrazolinates, particularly any one of mesotrione, tembotrione, isoxaflutole or bicyclopyrone. In another aspect, the disclosure provides for a composition comprising, consisting essentially of, or consisting of isoxaflutole, glyphosate, fomesafen, and salts thereof, for example, sodium salt of fomesafen, Balance® Bean (Bayer CropScience), Balance® 75 WG (Bayer CropScience), Cobra® (Valent), Laudis® (Bayer CropScience), Flexstar® GT (Syngenta), Flexstar® (Syngenta), Roundup® (Monsanto), and Roundup® PowerMAX (Monsanto) for use with any of the methods described herein.

In another aspect, the disclosure provides for use of two or more compositions described herein, for example, a first composition comprising, consisting essentially of, or consisting of (1) a HPPD inhibitor herbicide described herein, such as isoxaflutole, together with (2) a glyphosate-based composition or a glyphosate-based composition together with another active agent described herein, such as fomesafen. In an aspect, the combination composition of use of two compositions of (1) and (2) unexpectedly provides a synergistic or safening effect, thereby reducing damage to plants or crops.

In an aspect, the amount of a controlling, damage reducing, or yield increasing composition described herein can be an amount that is effective ("effective amount") to protect seeds, plant parts, or plants against damage or pest infestation and/or increase plant yield.

In an aspect, a composition or combination of compositions described herein are applied to soil, a plant, or a plant part from about 0.1-about 10 mg/ai, from about 0.1-about 5 mg/ai, from about 0.2-about 2 mg/ai, from about 0.025-about 1 mg/ai, from about 0.075-about 0.75 mg/ai, from about 0.05-about 0.5 mg/ai, from about 0.20 mg/ai to about 0.75 mg/ai, from about 0.05 mg/ai to about 0.75 mg/ai, or from about 0.2-about 1.0 mg/ai. In an aspect, a composition described herein is applied to soil, a plant, or a plant part from about 0.1-about 10 mg/ai, from about 0.1-about 5 mg/ai, from about 0.2-about 2 mg/ai, from about 0.1-about 1 mg/ai, from about 0.1-about 0.75 mg/ai, from about 0.2-about 1 mg/ai, from about 0.2-about 0.75 mg/ai, from about 0.05-about 1 mg/ai, from about 0.05-about 0.75 mg/ai, or about 0.20 mg/ai to about 0.75 mg/ai, about 0.05 mg/ai to about 0.75 mg/ai from about 0.25-about 0.5 mg/ai.

In an aspect, a composition or combination or compositions described herein are applied to soil, a plant, or a plant part (a) about 0.1-about 10 mg/ai, from about 0.1-about 5 mg/ai, from about 0.2-about 2 mg/ai, from about 0.2-about 1 mg/ai, from about 0.2-about 0.75 mg/ai, or from about 0.25-about 0.5 mg/ai of an HPPD inhibitor herbicide, isoxaflutole, and (b) about 0.1-about 10 mg/ai, from about 0.1-about 5 mg/ai, from about 0.2-about 2 mg/ai, from about 0.2-about 1 mg/ai, from about 0.2-about 0.75 mg/ai, or from about 0.25-about 0.5 mg/ai of an active agent described herein such as glyphosate and fomesafen.

In an aspect, a composition combination described herein is applied to soil, a plant, or a plant part from (a) about 0.1-about 10 mg/ai, from about 0.1-about 5 mg/ai, from about 0.2-about 2 mg/ai, from about 0.2-about 1 mg/ai, from about 0.2-about 0.75 mg/ai, or from about 0.25-about 0.5 mg/ai of an HPPD inhibitor herbicide, isoxaflutole and (b) about 0.1-about 10 mg/ai, from about 0.1-about 5 mg/ai, from about 0.2-about 2 mg/ai, from about 0.2-about 1 mg/ai, from about 0.2-about 0.75 mg/ai, or from about 0.25-about 0.5 mg/ai of an active agent described herein such as glyphosate and fomesafen.

In an aspect, the disclosure provides for an application rate of a composition or active agent described herein of about 5 to about 25 ounces/acre, about 10 to about 20 ounces/acre, about 10 to about 18 ounces/acre, about 12 to about 18 ounces/acre, about 15 to about 20 ounces per acre.

In another aspect, the disclosure provides for an of a composition or active agent described herein of about 0.2 to about 3 lb ai/acre; about 0.3 to about 2 lb ai/acre; about 0.2 to about 1 lb ai/acre; about 0.2 lb ai/acre, about 0.3 lb ai/acre, about 0.375 lb ai/acre, or about 0.5 lb ai/acre.

In another aspect, a composition described herein comprises an active agent described herein, for example of an HPPD inhibitor herbicide, isoxaflutole, glyphosate, and fomesafen in at least about 0.1%, at least about 0.25%, at least about 0.5%, at least about 1%, at least about 2% at least about 2.5%, at least about 5%, at least about 7.5%, at least about 10%, at least about 25%, or at least about 50%, by weight of a composition. In yet another aspect, a composition comprises an active agent described herein, for example, an HPPD inhibitor herbicide, isoxaflutole, glyphosate, and fomesafen that is no more than about 1%, no more than about 2.0%, no more than about 2.5%, no more than about 5%, no more than about 7.5%, no more than about 10%, no more than about 25%, no more than about 50%, by weight of a composition.

In another aspect, the disclosure provides for a composition comprising an active agent described herein, for example, an HPPD inhibitor herbicide, isoxaflutole, glyphosate, or fomesafen, at about 0.1% to about 1%, about 0.1% to about 2.5%, about 0.5% to about 2.5%, about 1% to about 2%, about 1% to about 3%, about 1% to about 5%, about 1% to about 10%, about 2% to about 10%, about 5% to about 10%, about 5% to about 20%, about 10% to about 25%, about 10% to about 50%, about 25% to about 50%, or about 20% to about 80%, and about 95% or more by weight of a composition. In another aspect, the disclosure provides for a composition comprising glyphosate at in an amount of about 0.1% to about 1%, about 0.1% to about 2.5%, about 0.5% to about 2.5%, about 1% to about 2%, about 1% to about 3%, about 1% to about 5%, about 1% to about 10%, about 2% to about 10%, about 5% to about 10%, about 5% to about 20%, about 10% to about 25%, about 10% to about 50%, about 25% to about 50%, or about 20% to about 80%, and about 95% or more by weight of a composition. In another aspect, the disclosure provides for a composition comprising fomesafen in an amount of about 0.1% to about 1%, about 0.1% to about 2.5%, about 0.5% to about 2.5%, about 1% to about 2%, about 1% to about 3%, about 1% to about 5%, about 1% to about 10%, about 2% to about 10%, about 5% to about 10%, about 5% to about 20%, about 10% to about 25%, about 10% to about 50% by weight of a composition.

In yet another aspect, the disclosure provides for a composition comprising glyphosate at in an amount of about 5% to about 20%, about 10% to about 25%, about 10% to about 50%, about 25% to about 50%, or about 20% to about 80%, and about 95% or more by weight of a composition. In another aspect, the disclosure provides for a composition comprising fomesafen in an amount of about 0.1% to about 1%, about 0.1% to about 2.5%, about 0.5% to about 2.5%, about 1% to about 2%, about 1% to about 3%, about 1% to about 5%, about 1% to about 10%, about 2% to about 10%, about 5% to about 10%, about 5% to about 20% by weight of a composition.

In an aspect, a composition or formulation described herein contain between 0.1 and 95 percent by weight of active. The active ingredient concentration can be about 5-25%, 10-50%, about 10-75%, about 20-50%, or about 5-90% by weight of the composition. The concentrations per liter of volume can be about 50-about 800 grams active per liter, about 100-about 700 grams active per liter, about 200-about 600, about 400-about 600, about 300-about 700 grams, about 400-about 800, about 600-about 800, about 600-about 700 grams active per liter. In an aspect, the composition can also include one or more chelating agents.

In an aspect, a composition described herein with an active agent described herein, can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is liquid solvents, pressurized liquefied gases and/or solid carriers, optionally with the use of surface-active agents, that is emulsifiers and/or dispersants and/or foam formers. If the extender used is water, it is also useful to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants, for example, lignosulphite waste liquors and methylcellulose are suitable.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

Colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc, can also be used.

Plants are understood as meaning, in the present context, all plants and plant populations, such as desired and undesired wild plants or crop plants (including naturally occurring crop plants). Crop plants or crops may be plants which can be obtained by conventional breeding and optimization methods or else by biotechnological and genetic engineering methods or by combinations of these methods, including the transgenic plants and including the plant varieties capable or not capable of being protected by plant breeders' rights.

The disclosure further provides for methods described herein where plants treated with compositions described herein are selected from one or more of soy, dry beans, snap beans, soybean, corn, vegetables, cereals (for example wheat, barley, rye, oats), rice, millet, or dicotyledonous farm crops, such as sugar beet, oilseed rape, cotton, sunflower and legumes, for example of the genera glycine (for example Glycine max. (soybean), such as non-transgenic Glycine max. (for example conventional cultivars, such as STS cultivars) or transgenic Glycine max. (for example RR soybean or LL soybean) and crossbreeds thereof), Phaseolus, Pisum, Vicia and Arachis, or vegetable crops from various botanical groups, such as potato, leek, cabbage, carrot, tomato, onion, and also permanent crops and plantation crops, such as pome fruit and stone fruit, berry fruit, grapevines, Hevea, bananas, sugar cane, coffee, tea, citrus fruit, nut plantations, lawn, palm plantations and forest plantations. In a particularly aspect, the disclosure further provides for methods described herein where seeds or plants treated with compositions described herein are soybean and corn.

In an aspect, a compound or composition described herein is formulated as a foliar composition, a foliar spray, solution, emulsion, coating formulation, non-pesticidal or pesticidal coating formulation, encapsulated formulation, solid, liquid, fertilizer, paste, granule, powder, suspension, or suspension concentrate. In another aspect, a compound or composition described herein may be employed alone or in solid, dispersant, or liquid formulation. In yet another aspect, a compound or composition described herein is formulated as a tank-mix product.

In another aspect, a compound or composition described herein can take any of a variety of dosage forms including, without limitation, suspension concentrates, aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspoemulsion concentrates, soluble concentrates, wettable powders, soluble powders, dusts and granules, water-soluble granules or tablets, water-soluble powders for the treatment of seed, wettable powders, natural products and synthetic substances impregnated with a compound or composition described herein, a net impregnated with a compound or composition described herein, and also microencapsulations in polymeric substances and in coating materials for seed, and also ULV cold-fogging and warm-fogging formulations.

In an aspect, a composition described herein can include Ammonium Sulfate (AMS), for example, liquid AMS, a Crop Oil Concentrate (COC) or Methylated Seed Oil (MSO), for example, a nonphytotoxic COC or MSO containing about 15-20% approved emulsifier at 0.5-1% v/v (2-4 quarts/100 gallons) of finished spray volume. COC, and/or a Nonionic Surfactant (NIS), for example, at least 80% active ingredient at 0.25-0.5% v/v (1-2 quarts/100 gallons) of finished spray volume. In an aspect, one or more of the above components may be added to a composition comprising, for example, isoxaflutole, glyphosate, and/or fomesafen.

In another aspect, a composition disclosed herein may optionally include one or more additional compounds providing an additional beneficial or otherwise useful effect. Such compounds include, without limitation, an adhesive, a surfactant, a solvent, a wetting agent, an emulsifying agent, a carrier, an adjuvant, a diluent, a dispersing agent an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, or any combination thereof. In an aspect, a composition described herein is odor free. In another aspect, the surfactant is Genapol, for example Genapol X-080.

In another aspect, a compositions described herein can be combined with a fertilizer. Examples of fertilizers capable of being used with the compositions and methods described herein include, for example, Urea, Ammonium Nitrate, Ammonium Sulfate, Calcium Nitrate, Diammonium Phosphate, Monoammonium phosphate, Triple Super Phosphate, Potassium Nitrate, Potassium nitrate, nitrate of potash, Potassium Chloride, muriate of potash, di and mono potassium salts of phosphite/phosphonate.

Kit

In another aspect, the disclosure provides for a kit comprising, consisting essentially of, or consisting of any of the compounds or compositions disclosed herein. In an aspect, the kit includes any of the combination of compounds or compositions described in Examples 1-5 or FIGS. 1-5. In another aspect, the kit provides for the compositions described in Examples 1-4 or FIGS. 1-5, applied in a manner that is consistent with the methodology of these examples and figures. In another aspect, the kit provides instructions or guidance regarding the use of the compositions or methods described herein.

In an aspect, the kit includes instructions describing the methodology described herein. In another aspect, the kit includes instructions describing the methodology set forth in any of Examples 1-4 or FIGS. 1-5. In an aspect, the instructions are included with the kit, separate from the kit, in the kit, or are included on the kit packaging.

The following examples serve to illustrate certain aspects of the disclosure and are not intended to limit the disclosure.

EXAMPLES

Example 1

Example 1 describes maximum phytotoxicity measurements for glyphosate tolerant soybean seeds treated with the application of compositions containing glyphosate and isoxaflutole.

Glyphosate tolerant soybean seeds are planted. At V2, compositions containing glyphosate and isoxaflutole are applied to soybean plants or plant parts. The soybeans are evaluated at 7, 14, and 35 days after application. In another aspect, compositions containing glyphosate and isoxaflutole are applied to soybean plants or plant parts at such a time when unwanted plant or weeds are prevalent during the growing process.

FIG. 2 describes the maximum phytotoxicity for Roundup® Ready soybean seeds treated with a Balance® Bean and Roundup at V2. The amount of Balance® Bean varies from 0, 0.0375, 0.07, 0.14, 0.275, 0.55, 1.1, 2.2, and 4.375 g ai/ha. The dose of Roundup® are maintained throughout each trial at 1543 g ai/ha.

Example 2

Example 2 describes maximum phytotoxicity measurements for glyphosate tolerant soybean seeds treated with the application of compositions containing glyphosate, isoxaflutole, and fomesafen.

Glyphosate tolerant soybean seeds are planted. At V2, compositions containing glyphosate, isoxaflutole, and fomesafen are applied to soybeans. The soybeans are evaluated at 7, 14, and 35 days after application.

Figure 3:
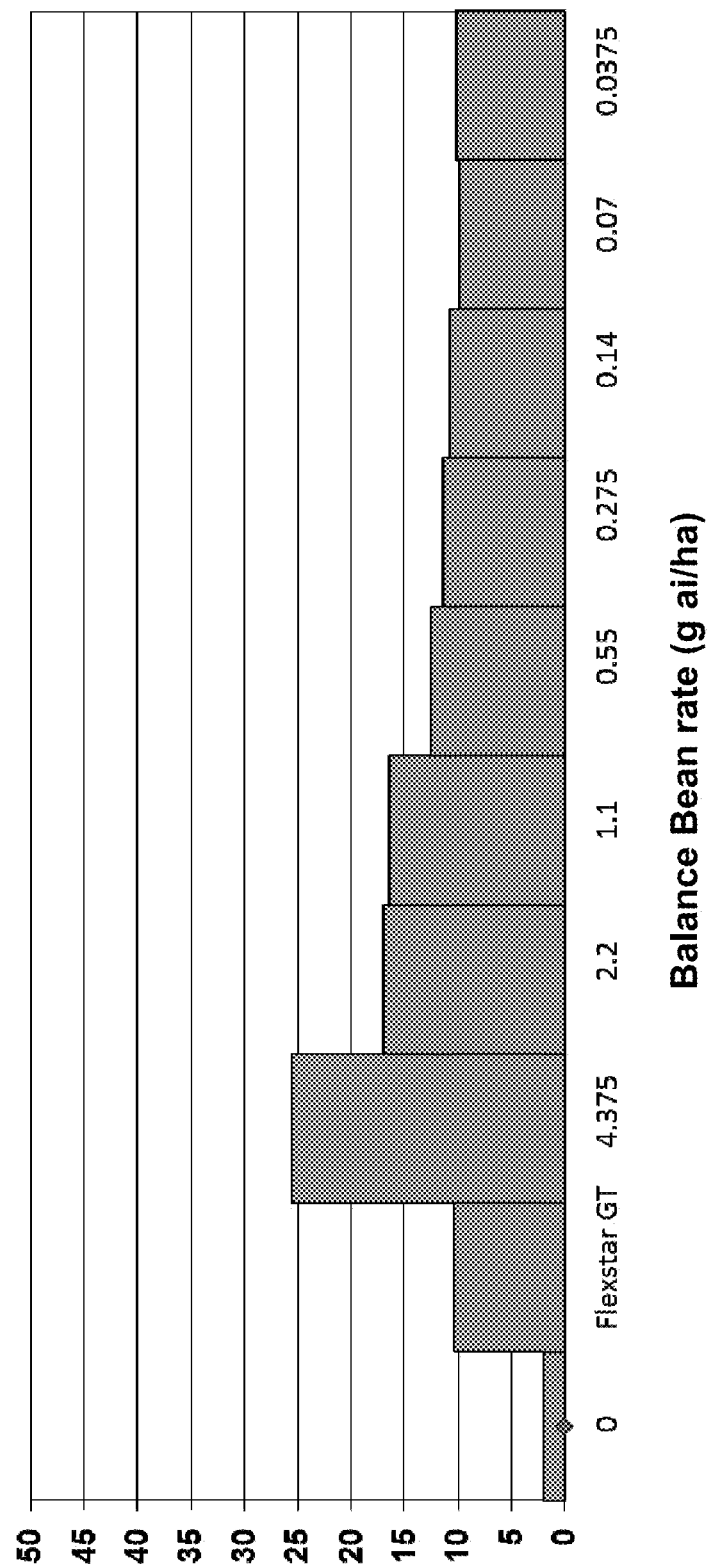
FIG. 3 sets forth the maximum phytotoxicity for Roundup® Ready soybean seeds treated with a Balance® Bean and Flexstar® GT at V2. The data represents the average of six trials. Max phytotoxicity (%) is represented in the Y axis.

FIG. 3 describes the maximum phytotoxicity for Roundup® Ready soybean seeds treated with a Balance® Bean and Flextstar® GT at V2. Balance® Bean contains isoxaflutole and Flextstar GT contains about 6.72% fomesafen by weight and about 25.6% Glyphosate by weight. The amount of Balance® Bean varies from 0, 0.0375, 0.07, 0.14, 0.275, 0.55, 1.1, 2.2, and 4.375 g ai/ha. The dose of Flextstar GT is maintained throughout each trial at 347 g ai/ha.

Example 3

Example 3 describes comparison maximum phytotoxicity measurements for glyphosate tolerant soybean seeds treated with (1) application of compositions containing glyphosate, isoxaflutole, and fomesafen and (2) the application of compositions containing glyphosate and isoxaflutole.

Glyphosate tolerant soybean seeds are planted. At V2, compositions containing (1) glyphosate, isoxaflutole, and fomesafen or (2) glyphosate and isoxaflutole are applied to soybeans. The soybeans are evaluated at 7, 14, and 35 days after application.

Figure 4:
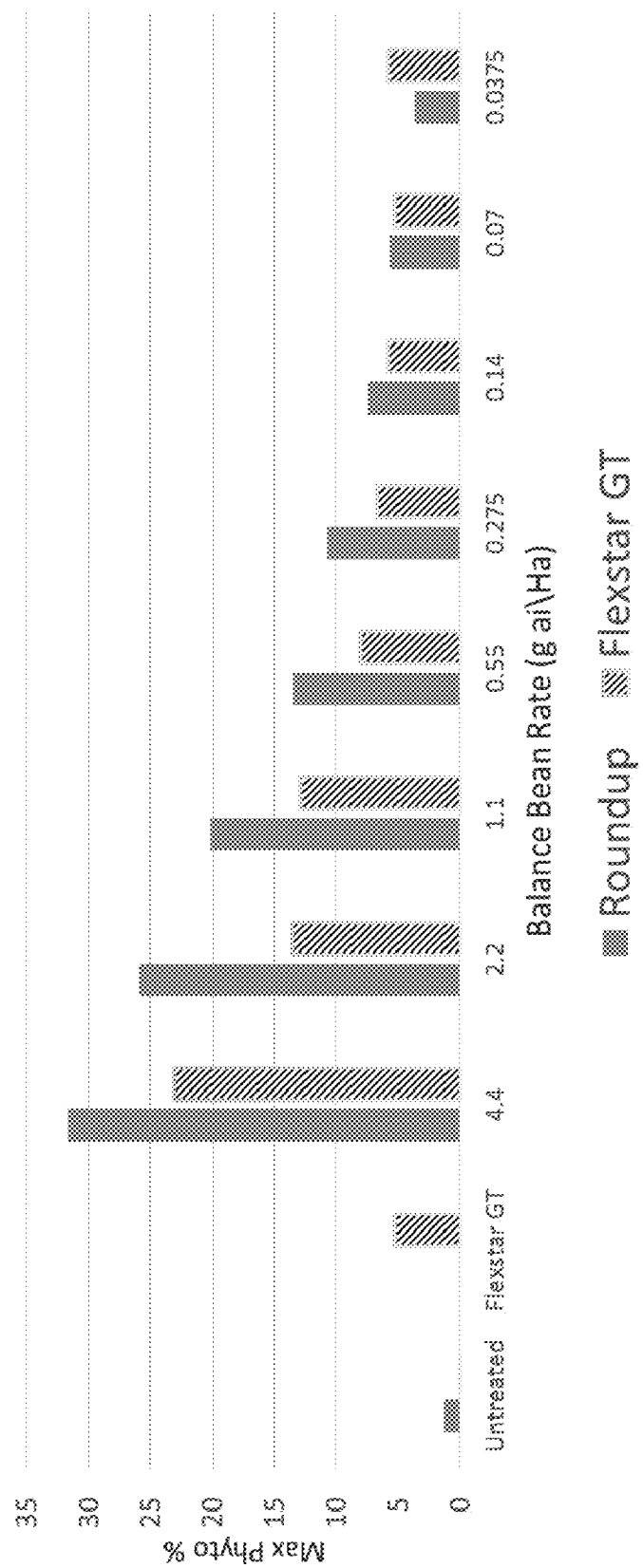
FIG. 4 sets forth maximum phytotoxicity for Roundup® Ready soybean seeds with an application of (1) Balance® Bean and Roundup® as compared to (2) Balance® Bean and Flexstar® GT measured 7-14 days after application.

FIG. 4 describes the maximum phytotoxicity for Roundup® Ready soybean seeds treated with (1) Balance® Bean and Flextstar GT at V2 or (2) Balance® Bean and Roundup® at V2. In each trial, the amount of Balance® Bean varies from 0, 0.0375, 0.07, 0.14, 0.275, 0.55, 1.1, 2.2, and 4.375 g ai/ha. The dose of Flextstar GT is maintained throughout each trial at 347 g ai/ha and the dose of Roundup® is maintained throughout each trial at 1543 g ai/ha.

As described in FIG. 4, the treatment of Roundup® Ready soybean seeds with (1) Balance® Bean (isoxaflutole) and Flextstar GT (glyphosate and fomesafen) at V2 unexpected resulted in lower phototoxicity as compared to (2) Balance® Bean (isoxaflutole) and Roundup® (glyphosate).

Example 4

Example 4 describes soybean yield measurements for glyphosate tolerant soybean seeds treated with (1) application of compositions containing glyphosate, isoxaflutole, and fomesafen and (2) the application of compositions containing glyphosate and isoxaflutole.

Glyphosate tolerant soybean seeds are planted. At V2, compositions containing (1) glyphosate, isoxaflutole, and fomesafen or (2) glyphosate and isoxaflutole are applied to soybeans. The soybeans are evaluated at 7, 14, and 35 days after application.

Figure 5:
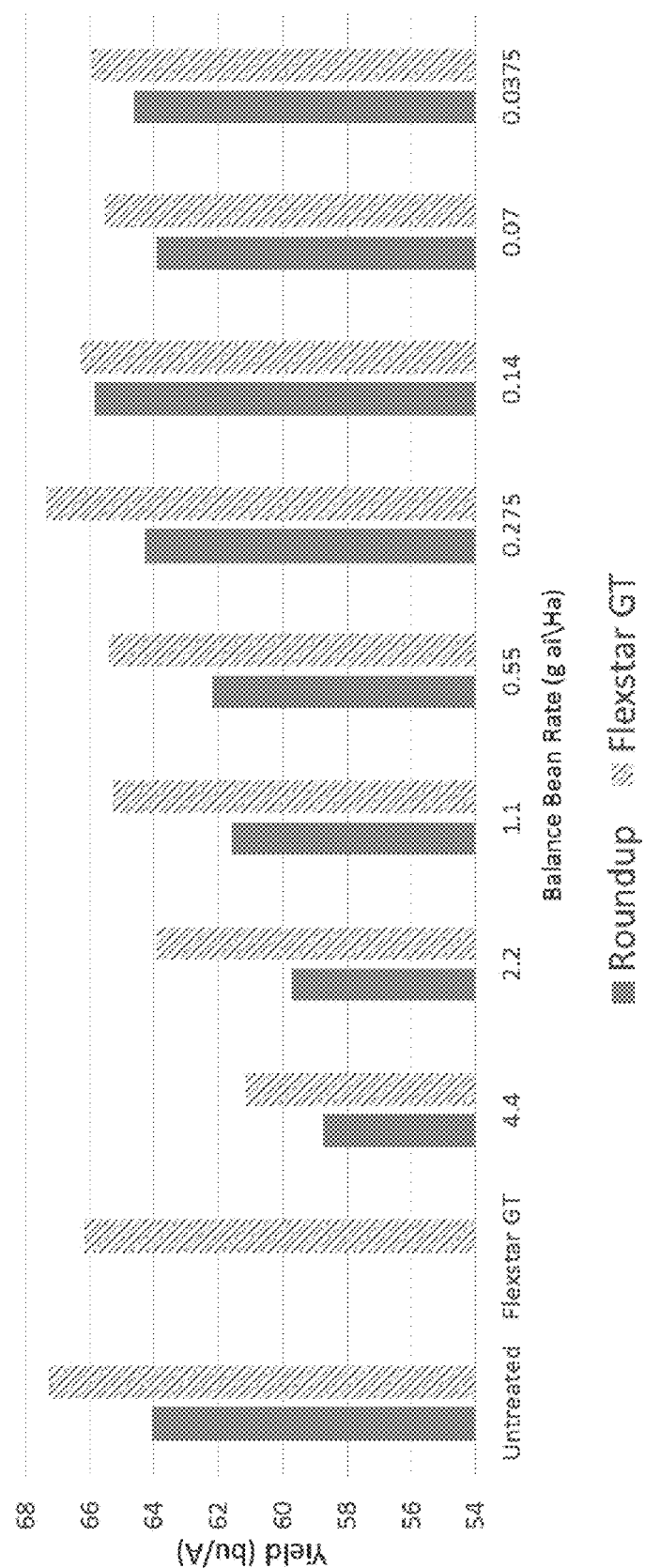
FIG. 5 sets forth soybean yield for Roundup® Ready soybean seeds with an application of (1) Balance® Bean and Roundup® as compared to (2) Balance® Bean and Flexstar® GT measured at 7-14 days after application.

FIG. 5 describes soybean yield for Roundup® Ready soybean seeds treated with (1) Balance® Bean and Flextstar GT at V2 or (2) Balance® Bean and Roundup® at V2. In each trial, the amount of Balance® Bean varies from 0, 0.0375, 0.07, 0.14, 0.275, 0.55, 1.1, 2.2, and 4.375 g ai/ha. The dose of Flextstar GT is maintained throughout each trial at 347 g ai/ha and the dose of Roundup® is maintained throughout each trial at 1543 g ai/ha.

As described in FIG. 5, the treatment of Roundup® Ready soybean seeds with (1) Balance® Bean (isoxaflutole) and Flextstar GT (glyphosate and fomesafen) at V2 unexpected resulted in a higher yield as compared to (2) Balance® Bean (isoxaflutole) and Roundup® (glyphosate). Based on the data of FIG. 5, Flextstar® GT appears to safen soybeans from Balance® Bean yield reduction in an unexpected manner.

The invention claimed is:

1. A method for controlling, mitigating, or reducing weed infestation and/or damage in a glyphosate tolerant or resistant seed, plant, or crop, comprising treating soil, a plant, and/or a plant part with as the sole herbicides:
  a) a HPPD inhibitor herbicide;
  b) glyphosate; and
  c) fomesafen,
wherein said HPPD inhibitor herbicide is selected from the group consisting of mesotrione, tembotrione, isoxaflutole, and bicyclopyrone and wherein the presence of fomesafen with said a and b increases crop yield and lowers the phytotoxicity relative to said a and b combined.

2. The method according to claim 1, wherein the herbicides are applied as a treatment to plant or plant parts.

3. The method according to claim 1, wherein said herbicides are applied to glyphosate tolerant or resistant soybean seed.

4. The method according to claim 1, wherein said method further results in increased control or reduction of weed infestation relative to the application of a HPPD inhibitor herbicide and glyphosate.

5. The method according to claim 1, wherein said method results in a plant or crop yield increase relative to the application of a HPPD inhibitor herbicide and glyphosate.

6. The method according to claim 1, wherein said method results in decreased damage to a plant or crop relative to the application of a HPPD inhibitor herbicide and glyphosate.

7. The method according to claim 1, wherein said HPPD inhibitor herbicide is isoxaflutole.

8. The method of claim 1, wherein said HPPD inhibitor herbicide is applied to seed plant, or plant part at a rate of from about 0.01 to about 5 g ai/ha.

9. The method of claim 8, wherein said iHPPD inhibitor herbicide is applied to a seed, plant, or plant part at a rate of from about 0.01 to about 2 g ai/ha.

10. The method of claim 9, wherein said HPPD inhibitor herbicide is applied to a seed, plant, or plant part from about 0.03 to about 0.5 g ai/ha.

11. The method according to claim 8, wherein said HPPD inhibitor herbicide comprises isoxaflutole.

12. The method of claim 1, wherein a), b) and c) are treated at the V2 stage.

13. The method of claim 1, wherein a), b), and/or c) are present in one or more different compositions and applied sequentially or simultaneously.

14. A treated plant or plant part comprising as the only herbicides:
a) a HPPD inhibitor herbicide selected from the group consisting of mesotrione, tembotrione, isoxaflutole, and bicyclopyrone;
b) glyphosate; and
c) fomesafen and wherein the presence of fomesafen with said a and b increases crop yield and lowers the phytotoxicity relative to said a and b combined.

15. The treated plant or plant part of claim 14, wherein said treated plant or plant part is soybean plant or plant part.

16. The treated plant or plant part of claim 14, wherein said treated plant or plant part is glyphosate tolerant or resistant.

17. The treated plant or plant part according to claim 14, wherein said HPPD inhibitor herbicide is isoxaflutole.

18. The treated plant or plant part of claim 16, wherein said treated plant or plant part is a soybean seed.

19. A herbicidal composition comprising as the only herbicides isoxaflutole, glyphosate, and fomesafen.

* * * * *